United States Patent [19]

Rauchwerger

[11] 3,958,159

[45] May 18, 1976

[54] CAPACITANCE PROBE AND SYSTEM FOR PRECISION MEASUREMENT OF LIQUID LEVEL

[76] Inventor: George P. Rauchwerger, c/o Expo Instruments Inc., 183-D Commercial Ave., Sunnyvale, Calif. 94086

[22] Filed: Dec. 26, 1974

[21] Appl. No.: 536,347

Related U.S. Application Data

[63] Continuation-in-part of Ser. No. 309,735, Nov. 27, 1972, Pat. No. 3,864,974, which is a continuation-in-part of Ser. No. 105,254, Jan. 11, 1971, Pat. No. 3,710,244.

[52] U.S. Cl. ............................. 317/246; 73/304 C; 324/61 P
[51] Int. Cl.² ........................................ G01F 23/26
[58] Field of Search ................. 324/61 P, 61 R; 73/304 C, 304 R; 317/246; 242/147 R, 75

[56] References Cited
UNITED STATES PATENTS

| | | |
|---|---|---|
| 2,817,234 | 12/1957 | Campbell .......................... 324/61 P |
| 2,836,739 | 5/1958 | Mesh ................................. 73/304 C |
| 3,188,865 | 6/1965 | Frost ................................. 73/304 C |

*Primary Examiner*—S. Clement Swisher
*Assistant Examiner*—Denis E. Corr
*Attorney, Agent, or Firm*—Julian Caplan

[57] ABSTRACT

The capacitance probe consists of a vertical insulated wire stretched taut in the tank, or other container, where liquid level is to be measured. Fittings at the top and bottom conveniently and efficiently support and tighten the wire. The system comprises an oscillator which impresses a sinusoidal voltage in series with the probe, preferably through a transformer so that there are no active electronics at the probe. One end of the probe is at ground potential. A long transmission line may connect the probe to the measuring electronics.

7 Claims, 12 Drawing Figures

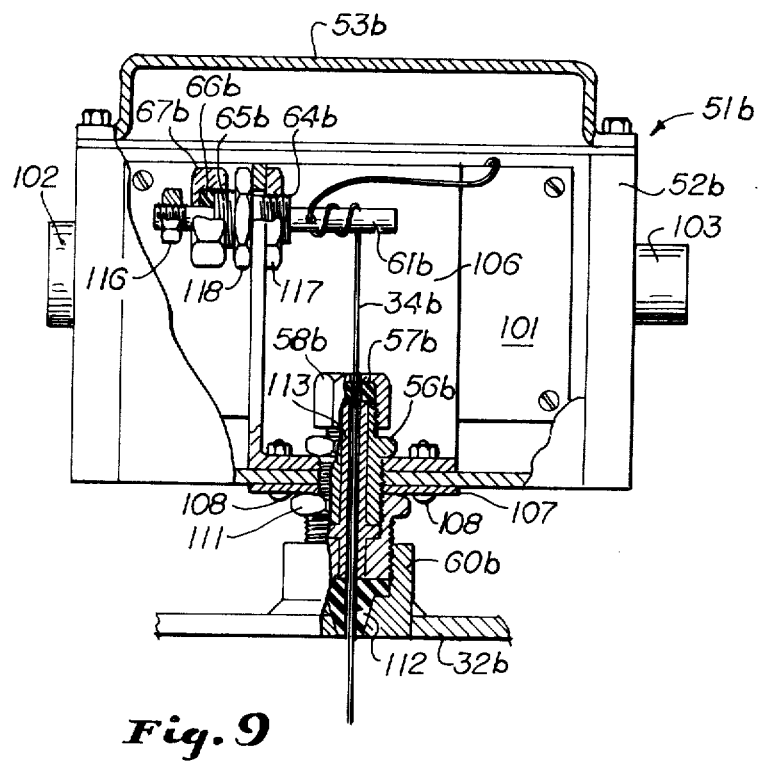
Fig. 9
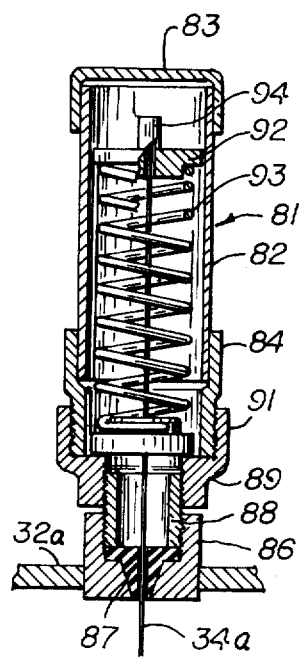
Fig. 8
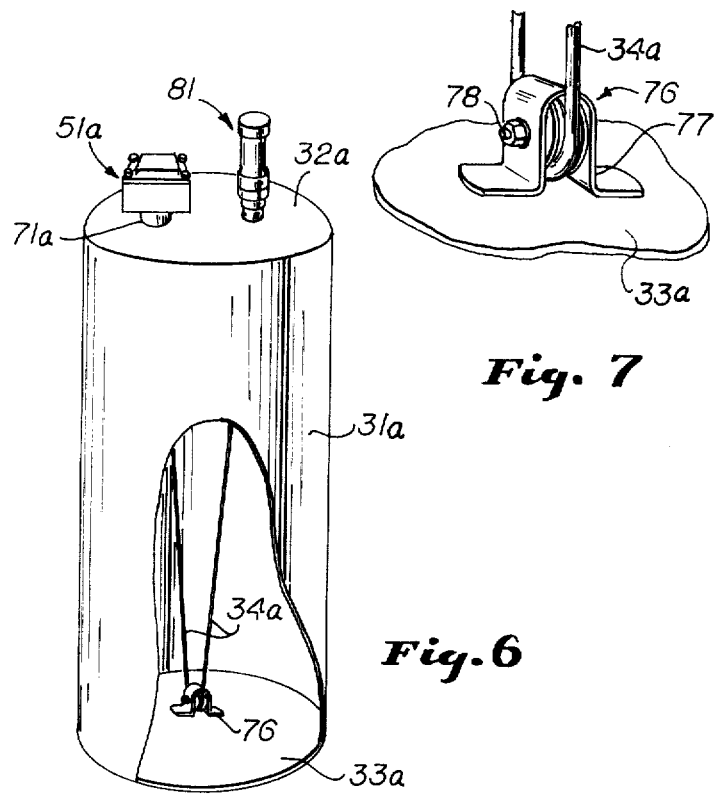
Fig. 7
Fig. 6

CAPACITANCE PROBE AND SYSTEM FOR PRECISION MEASUREMENT OF LIQUID LEVEL

This application is a continuation-in-part of Ser. No. 309,735, filed Nov. 27, 1972, now U.S. Pat. No. 3,864,974 which was a continuation-in-part of Ser. No. 105,254, filed Jan. 11, 1971, now U.S. Pat. No. 3,710,244.

A principal object of the present invention is to provide a simple, reliable and accurate means to measure the level of liquids in a tank, reservoir, etc., and to display the measurement directly in engineering units such as feet, meters, etc. The system employs no moving mechanical parts.

One of the features of the invention is the provision of a probe which is simple to install, is chemically inert, has no moving parts and is intrinsically safe so that it will not cause explosions or fire. A feature of the invention is the fact that there are no active electronic components at the probe head and there is no power at the probe head so that the danger of explosions and fire is minimized.

In one form of the invention there are no weights, and in the invention there are no floats, all of which are undesirable features of prior liquid measuring systems.

Other objects of the present invention will become apparent upon reading the following specification and referring to the accompanying drawings in which similar characters of reference represent corresponding parts in each of the several views.

In the drawings:

FIG. 6 is a view similar to FIG. 3 of a modification of the invention.

FIG. 7 is an enlarged fragmentary perspective view of a portion of FIG. 6.

FIG. 8 is an enlarged sectional view of a portion of FIG. 6.

FIG. 9 is a view similar to FIG. 4 of a further modification.

Essentially the system of the present invention comprises a capacitance probe 11, a measuring circuit indicated generally at 12, an oscillator 13 and a display, or control, device 14. The liquid level measuring system is claimed in Ser. No. 309,735 and it will be understood that the probe hereinafter disclosed and claimed is not limited to use in that system.

Oscillator 13 impresses a sinusoidal voltage in the range of 10 to 30 Khz in series with the capacitance probe 11. The probe 11 is located vertically in a container such as the tank 31 of FIG. 3, a reservoir or other location having a fluctuating liquid level. As liquid moves up or down the probe, the probe capacitance varies in direct proportion to the liquid covering the probe. Since the probe capacitance ($Cx$) is effectively in series with the oscillator 13 and a charge amplifier A1, the energy transferred from the oscillator 13 to amplifier A1 is directly proportional to the variation of $Cx$. The output of the ampifier A1 is then equal to the inverse ratio of the feedback capacitor ($Cf$) and the probe capacitor ($Cx$). Therefore, $Vo=Cx$ divided by $Cf$.

Theoretically, the output of amplifier A1 is then connected to a precision peak detector A2 and then to a display, or control, device 14, which can be calibrated to read any desired units such as feet or meters or to control any desired function as by means of a solenoid valve control (not shown) or the like. It has been found as a matter of practice, however, that the foregoing simplified circuit does not yield precise results. The present invention provides a practical, yet precise, instrument for such purpose.

Figure 2B:
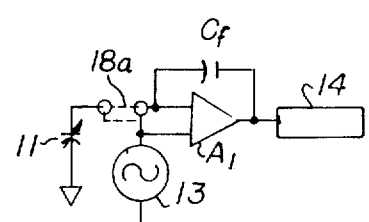
FIGS. 2A and 2B are more elementary schematics.
Figure 2A:
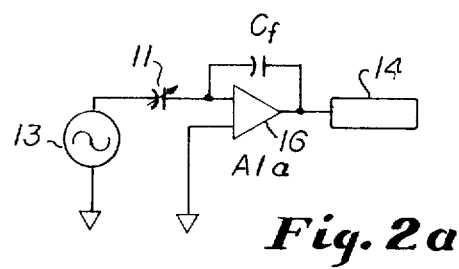
Figure 2:
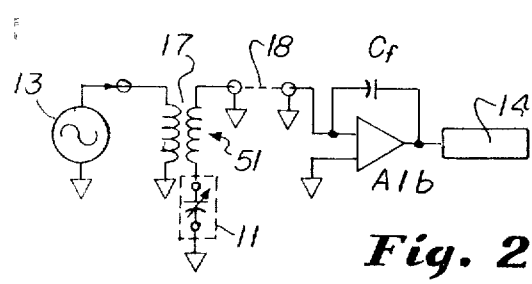
FIG. 2 is a simplified schematic of a preferred form of the invention.

Referring to FIG. 2A, this figure represents an equivalent circuit for ideal situations, such as where there are very short leads between the probe and the display. However, the system is not suitable where the probe capacitor must be at ground potential, such as in the present invention. Furthermore, a long wire must be connected from the probe capacitor to the measuring circuit without affecting the capacitance to be measured, and at the same time, to make the stray capacitances as low as possible. Referring to FIG. 2, an equivalent circuit is shown which is more in keeping with the requirements of the present invention. A ferrite potcore transformer 17 is placed in the probe head 51 which is mounted at one end of the probe 11. Transformer 17 provides the desired results without resorting to placing active electronics at the probe. Transformer 17 effectively places the oscillator 13 in series with the probe 11. It allows the end of the probe to be at ground potential. It allows long transmission lines 18 (1,000 feet or more) to be connected between the probe head 51 and the measuring electronics, all without deterioration in accuracy.

FIGS. 2B is another way of accomplishing results similar to that of FIG. 2 but the accuracy is not as good for large values of probe to liquid capacitance.

Figure 1:
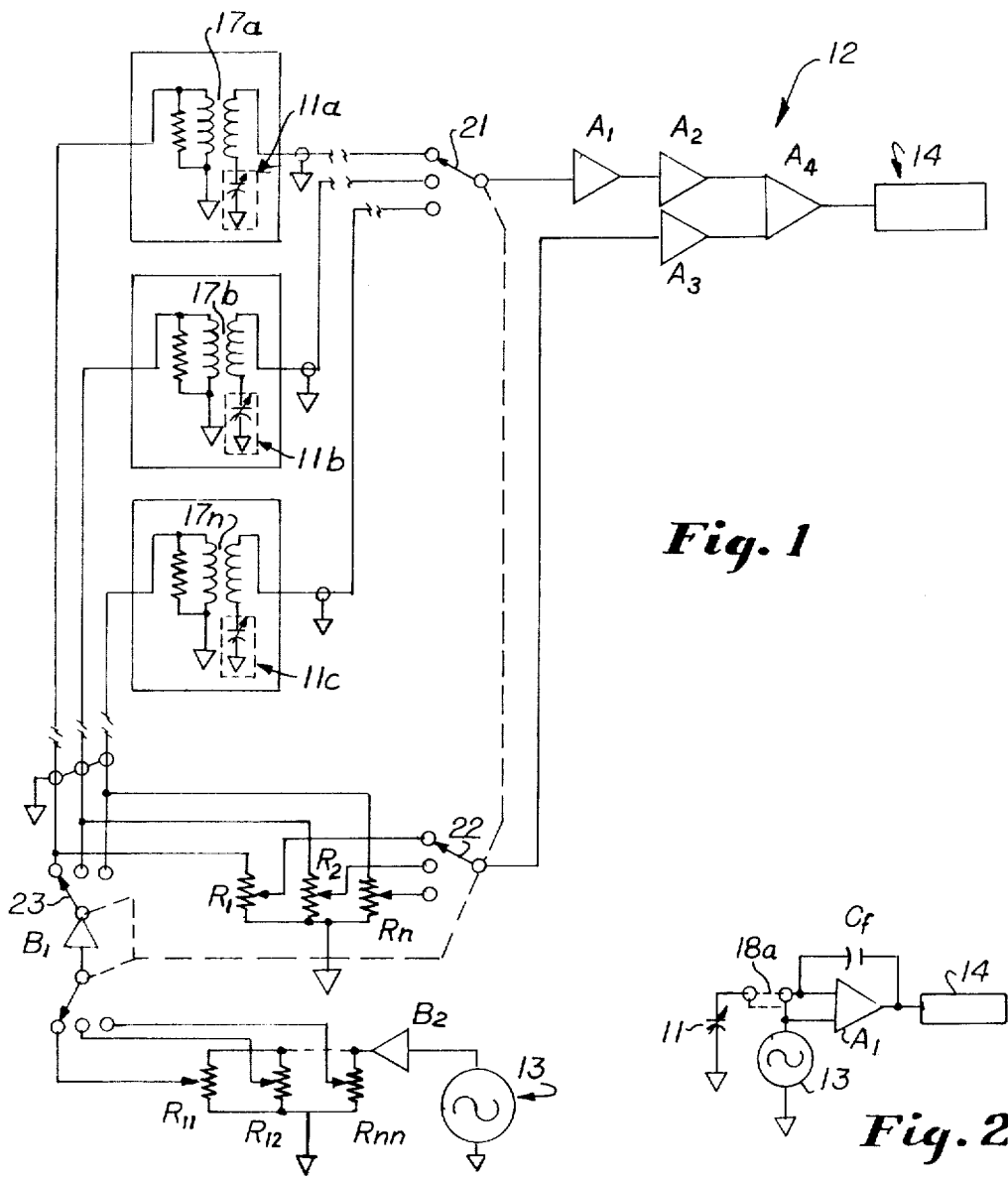
FIG. 1 is a schematic circuit diagram of one form of the invention showing a plurality of probes located at a distance with centralized measuring and display or control.

Directing attention now to the preferred embodiment of FIG. 1, the signal passing through the charge amplifier A1 is detected by detector A2 and amplified by amplifier A4. It is then read on a meter 14 or used to control some function such as a valve. However, this simplified version does not yield a precise measurement, since it does not take into account stray capacitances of the probe, there is no zero reference, and calibration is most difficult.

To provide a zero reference, proper calibration, and nulling of stray capacitances when the tank is empty, a second detector A3, a differential amplifier A4 and proper buffer amplifiers B1 and B2 are added. Detector A3 rectifies a portion of the outgoing oscillator signal. It tracks this signal whenever its amplitude is changed. This is necessary to calibrate the system. When the tank is emptied, the desired output at display 14 is zero. Setting at zero is accomplished by adjusting the zero calibration controls R1, R2, RN depending upon the number of probes being used. When the tank is full, the maximum reading is then calibrated by varying the oscillator amplitude controls R11, R12, RNN. This adjustment must be independent of the zero adjustments; and, therefore, it is necessary to track the oscillator. In effect by doing so, the difference between the outputs of the two detectors is always zero when the tank is empty or at the zero level condition. With this in mind, a differential amplifier A4 is used to measure the true value of the probe capacitance; and in turn, the actual liquid level.

Once the system has been calibrated for zero and maximum, to the desired reading in feet, centimeters, etc., it will measure the exact liquid level, since the difference between zero and maximum is a perfectly linear function. Because of the above features, the system lends itself well to a centralized, multiple tank liquid level measuring instrument. The switching from station to station is accomplished as shown in FIG. 1, it being understood that the four switches 21–24 are mechanically or electrically interconnected for turning together.

Display device 14 may be an analog or digital volt meter in the range of 1–10 volts dc. Instead of, or as a supplement to the display device 14, a control device may be any solid state or electro-mechanical device with a compatible input voltage to operate pumps, gates, or any function desired.

By using a digital voltmeter as a display, it can also serve as an interface to a computer, since most such digital voltmeters have binary decimal outputs.

PROBES

Figure 5:
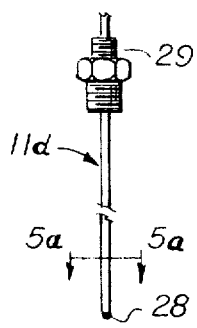
FIG. 5 is a schematic view showing a more elementary probe than is shown in FIG. 4.
Figure 5A:
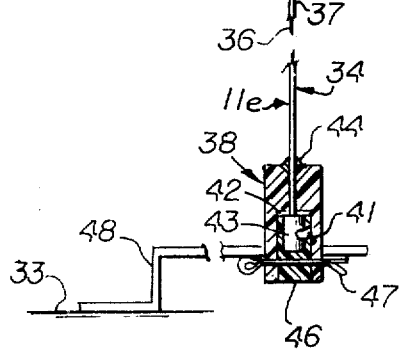
FIG. 5A is an enlarged cross-sectional view taken substantially along the line 5A—5A of FIG. 5.
Figure 5A:
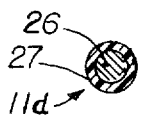

Preferred probes for the foregoing described system are other features of this invention. For small tanks, as shown in FIGS. 5, 5A, in range of up to 10 feet in height, a semi-rigid probe made of 3/16 to ¼ inch brass, or stainless steel, rod 26 is inserted into a tight-fitting, thin-walled Teflon tube 27 to act as an insulator and to provide corrosion resistance. The bottom end of probe 11d is hermetically sealed with epoxy 28 after the Teflon is properly etched. The top of the probe is received in a suitable fitting 29 for mounting in the top of a tank and for electrical connection.

Figure 3:
FIG. 3 illustrates in perspective a typical container in which one form of the invention may be installed, partly broken away to reveal interior construction.
Figure 4:
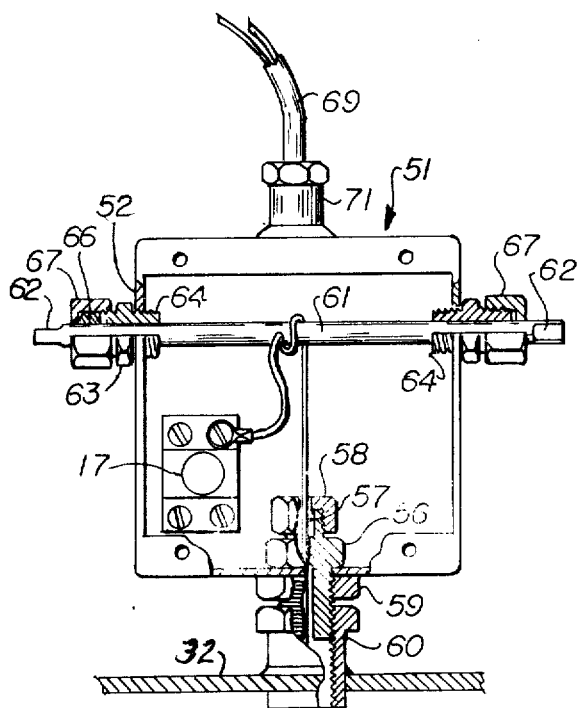
FIG. 4 is an enlarged sectional view showing a probe lower end and head in accordance with the present invention.

For large tanks of excess or ten feet), as shown in FIGS. 3 to 5A, inclusive, a flexible probe such as 11e is employed. In FIGS. 3 and 4 probe 11e consists of the probe proper which may be wire 34, a probe seal or plug 38, and a probe head 51.

Wire 34 has copper strands, or stainless steel core 36 insulated with a suitable chemically inert insulation 37, such as TEFLON or TEFZEL, the insulation being between 10 and 15 mils thick. The bottom of wire 34 is sealed by seal 38 hereinafter explained.

The plug 38 is machined from a piece of teflon rod approximately ½ inch in diameter and 1¼ inch long. A counterbored hole 41 is formed in the bottom and a countersink at the top. The end of wire 34 is stripped about ¼ inch and is inserted through the small hole in plug 38 and thence through a stainless steel washer 42 and a crimp ferrule 43 which is crimped about the end of the wire and holds it securely. This structure relieves strain and holds the wire inside the plug when it is under tension. Before the teflon surfaces are sealed, they are etched with a commercially available chemical to provide proper bonding. The wire 34 is pulled tight so that washer 42 is in close contact with the shoulder in the bore 41. The inside of the bore 41 is completely filled with a high strength semi-flexible epoxy filler 46. The countersunk portion at the top of the plug is filled with epoxy 44 forming a seal around the wire protruding from the plug. After the epoxy 46 has hardened, a transverse hole is drilled to accept cotter pin 47 to secure the probe to its anchor 48. The anchor 48 may be a flat leaf spring bent in Z shape as shown in FIGS. 3 and 4, one end of the spring being welded to the bottom 33 of the tank 31. The plug 38 is passed through a hole in the free end of spring 48 and the cotter pin 47 used to secure the plug 38 in place. The spring 48 (which is preferably corrosion resistant) provides strain relief for the probe to protect from varying conditions in the tank and also to provide constant tension on the probe. Where it is not possible to anchor the probe on the bottom, weight is placed on plug 38 to maintain proper tension on the probe.

Probe head 51 is secured to the top 32 of tank 31. It functions to support the probe and to apply tension to the probe as well as to provide a pressure seal at the top of the tank. It provides a terminal for the transmission lines in a weatherproof housing and the line transformer may be installed therein if desired. A preferred form of probe head 51 consists of a casing 52 which is closed by a cover 53 with a hermetic seal. The probe wire 34 is brought up into the casing 52 through a fitting 56 which is threaded into an internally threaded bushing 60 welded to the top 32 on tank 31 or other means whereby a tight seal is effected between the fitting 56 and the top 32. A Teflon ferrule 57 is slipped over the outside of the wire 34 interiorly of housing 52. Hollow nut 58 is threaded on to the upper end of fitting 56; and as it is tightened, the ferrule 57 is squeezed so that a thoroughly tight seal is accomplished. This seal is effective against pressure, liquid and gas. At the time the ferrule 57 is squeezed, the wire 34 has been drawn taut as hereinafter explained.

A transverse shaft 61 is mounted in casing 52 and a hole is drilled therein through which the wire 34 fits. By turning shaft 61, wire 34 is drawn taut until proper tension is reached. Hollow nut 58 is then tightened to squeeze pressure seal 57, as heretofore explained. The flattened end 62 of rod 61 extends exteriorly of casing 52. A double-end threaded fitting 63 is provided, the threads 64 engaging threaded holes in casing 52. Externally of casing 52 a compressible brass ferrule 66 is slipped over the shaft 61, and on the outside of ferrule 66 is a hollow nut 67. When nut 67 is tightened, the ferrule 66 is distorted, causing it to thereafter permanently turn with shaft 61. By tightening nut 67, the shaft 61 may be tightened or loosened. A duplicate of the construction on the left-hand end of the head 51 may be provided or the ferrule 66 may be omitted. Alternatively, the opposite fitting may have an O-ring which acts as a friction clutch and water seal. The probe wire 36 is connected to transformer 17 and thence connected to lead wire 69 through standard fitting 71.

FIG. 6 shows a modified installation wherein the wire 34a extends from the probe head 51a at the top 32a of tank 31a down to a pulley 76 of insulating material such as Delrin or Teflon fixed to the bottom 33a of tank 31a and thence up through the top 32a to a shock absorber 81. This arrangement simplifies manufacture and installation. Shock absorber 81 maintains constant tension on the wire 34a. Further, it protects the wire from damage due to turbulence in the liquid in the tank or from damage from accidental bumping by persons entering the tank.

The pulley 76 is mounted on bottom 33a by means of bracket 77 and pin 78. It will be understood that other pulley means may be employed.

Shock absorber 81 comprises a housing 82 having a hermetically sealed cap 83 at its upper end. The lower end of housing 82 is received in an adapter 84 (also hermetically sealed thereto). Lower reducer coupling 86 is welded or otherwise permanently secured surrounding a hole in top 32a. In the bottom of coupling 86 is a pressure seal 87 engaged by a nipple 88 which is threaded into the interior of coupling 86 and bears against the seal 87. Seal 87 is required in the food industry and other installations where sanitation is a problem. It serves to seal gases and liquids and also prevents bacteria from forming inside housing 82. Adapter 84 is threaded into upper reducer coupling 89 which is threaded onto the upper end of nipple 88. Within housing 82 are a lower shoulder washer 91, an upper shoulder washer 92 and a coil spring 93 interposed there-between. The upper end of wire 34a passes through the pressure seal 87 and thence up through washers 91, 92 and spring 93 and is held in place by a crimp connector 94 so that the spring 93 is normally under some compression. Spring 93 flexes with temperature changes and also compresses in event of a strain being imposed on wire 34a as has heretofore been explained. Many of the elements of FIG. 6 are similar to those of the preceding modifications and the same reference numerals followed by the subscript a are used to designate corresponding parts.

Directing attention to FIG. 9, a modified probe head 51b is illustrated. In this modification, the casing 52b is open at the top and closed by a water-tight lid 53b, the casing and lid preferably being formed of a material such as fiberglass. The modification of FIG. 9 is simpler than that of FIG. 4, consisting of fewer parts. Within casing 51b there may be installed a plate 101 for mounting printed circuit boards if desired. The casing is further provided with an air vent 102 and has a hub 103 for external wire connections.

A right angle mounting bracket 106 is fastened to the bottom of casing 52b, strengthened by plate 107, by means of screws 108. Externally threaded fitting 56b passes through holes in bracket 106, housing 51b and plate 107 and is held in place by pressure tight connector 111, which is threaded into bushing 60b, welded or otherwise secured surrounding a hole in top 32b. Inside bushing 60b is a seal 112 which acts as a pressure seal and at the same time prevents bacteria from forming inside housing 52b. Sleeve 113 bears against seal 112 and compresses the same against the wire 34b and also extends up through fitting 56b. At its upper end is a second pressure seal 57b. Nut 58b threaded onto the exterior of fitting 56b compresses seal 57b against wire 34b and against sleeve 113.

Hollow compression fitting 63b is mounted horizontally extending through a hole in bracket 106. Fitting 63b is threaded at either end and intermediate thereto is an enlarged head 118. Rod 61b, of an insulating material such as Delrin, fibreglass, etc., passes through fitting 63b. Threaded onto one end of rod 61b is a nut 116 which serves as a means of tightening the rod 61b and preferably tightens the same in one direction only in order to prevent mistakes during installation. On the outer end of fitting 63b is a compression ferrule 66b and threaded onto the exterior of fitting 63b is a hollow compression nut 67b. By turning nut 67b relative to head 118, the ferrule 66b tightens on rod 61b so that the assembly turns together. The end of fitting 63b opposite nut 67b passes through a hole in bracket 106 and is held in place by means of a holding nut 117.

Wire 34b extends up from nut 58b and passes through a hole in rod 61b and is wrapped around 61b. By turning nut 116 the tension on wire 34b is adjusted. When adequate tension is obtained, nut 67b is tightened, thus distorting ferrule 66b. This holds rod 61b in its position of adjustment. If it is necessary to readjust the tension, nut 67b is loosened and the procedure is repeated.

Casing 52b may be vented to provide air cirulation for warm electronic components. Vent 102 is preferably baffled and of a splash proof design to allow wires to pass through the box.

In the modification of FIG. 7, all measuring of liquid level may be accomplished at the probe head 51b, thus eliminating the need for coaxial wires. The leadout and power supply may be situated at a remote location and connected to the probe head 51b by shielded multiconductor wire. The system is thus computer compatible since the signal of each tank in a system, indicating liquid level in such tank, is presented continuously. Since signals are processed directly at each tank, control devices may be coupled to the system for controlling various functions via pumps, solenoid valves, actuators, proportional flow means, etc.

Many of the elements of FIG. 9 are similar to those in the preceding modifications and the same reference numerals followed by the subscript b are used to indicate corresponding parts.

Applications of the system are numerous. A principal application is measuring the height of liquid in wine and champagne tanks where it is difficult to measure the quantity of wine in a very large steel pressurized tank, or in very heavy liquids. Accurate inventory is essential in this and similar industries. Other applications include measurement and control of liquid levels in water pollution control, dairies, breweries, distilleries, chemical processing plants, etc.

What is claimed is:

1. A probe of the character described comprising a flexible wire metallic member, insulation surrounding said metallic member and mounting means for holding said probe taut in a container of liquid to be measured, said mounting means comprising anchoring means anchoring a first end of said wire and a head for a second end of said wire securing said wire taut, said head comprising a water-tight casing, a winch rotatable in said casing to which said first end of said wire is attached, said winch adjusting the tension of said wire and a seal on said casing through which said wire passes.

2. A probe according to claim 1 in which anchoring means comprises a hollow attachment plug, means securing said first end of said wire inside said plug, said plug forming a watertight connection with said insulation, and spring means attached to said plug pulling said wire taut.

3. A probe according to claim 1 in which said seal comprises a fitting in said casing having a threaded end, a hollow nut and a compressible sleeve between said nut and said fitting, said wire passing through said fitting, said sleeve and said nut, said nut when tightened on said threaded end compressing said sleeve to tighten around said wire to form a pressure and liquid-tight seal.

4. In combination a tank and a probe mounting according to claim 3 in which said head is mounted on the top of said tank with a water-tight pressure seal, said wire stretched taut in said tank, and said anchoring means fixed to said tank.

5. The combination of claim 4 in which said anchoring means comprises a hollow plug, a ferrule tight about said wire inside said plug with a water-tight and pressure-tight connection with said insulation and spring means gripping said plug and fixed to the interior of said tank, pulling down on said wire to maintain said wire taut.

6. A probe of the character described comprising a flexible wire metallic member, insulation surrounding said metallic member and mounting means for holding said probe taut in a tank of liquid to be measured, said mounting means comprising anchoring means anchoring a first end of said wire and a head for a second end of said wire securing said wire taut, said mounting means comprising a pulley, means for mounting said pulley in said tank, and a tension device, said wire passing from said head around said pulley and said first end received in said tension device, said tension device being located remote from said pulley.

7. A probe according to claim 6 in which said tension device is located on said tank and comprises a casing, a spring in said casing, means connected to said wire arranged to flex said spring as said wire is stressed, and sealing means sealing said casing to an aperture in said tank through which said wire passes into the interior of said casing, said sealing means permitting inward and outward movement of said wire relative to said casing as said wire is stressed.

* * * * *